(12) United States Patent
Zombo

(10) Patent No.: US 7,176,681 B2
(45) Date of Patent: Feb. 13, 2007

(54) INSPECTION OF COMPOSITE COMPONENTS USING MAGNETIC RESONANCE IMAGING

(75) Inventor: Paul John Zombo, Cocoa, FL (US)

(73) Assignee: Siemens Power Generation, Inc., Orlando, FL (US)

( * ) Notice: Subject to any disclaimer, the term of this patent is extended or adjusted under 35 U.S.C. 154(b) by 102 days.

(21) Appl. No.: 11/075,674

(22) Filed: Mar. 8, 2005

(65) Prior Publication Data

US 2006/0206025 A1    Sep. 14, 2006

(51) Int. Cl.
*G01V 3/00*    (2006.01)

(52) U.S. Cl. .................. 324/301; 324/307; 324/309

(58) Field of Classification Search .................. 324/301
See application file for complete search history.

(56) References Cited

U.S. PATENT DOCUMENTS

| | | | |
|---|---|---|---|
| 3,449,664 A | 6/1969 | Smith | |
| 4,495,466 A | 1/1985 | Lakin | |
| 4,625,168 A * | 11/1986 | Meyer et al. | 324/300 |
| 4,916,392 A | 4/1990 | Sendeff et al. | |
| 4,949,041 A | 8/1990 | Zur | |
| 4,998,065 A | 3/1991 | Koizumi | |
| 5,905,376 A | 5/1999 | Synderman et al. | |
| 6,150,809 A | 11/2000 | Tieman et al. | |
| 6,437,565 B1 | 8/2002 | Early et al. | |
| 6,541,973 B1 | 4/2003 | Danby et al. | |
| 6,600,317 B1 | 7/2003 | Kumai et al. | |
| 6,611,144 B2 | 8/2003 | Abe | |
| 6,714,807 B2 | 3/2004 | Zur | |
| 6,728,568 B1 | 4/2004 | Yatsui et al. | |
| 6,737,865 B2 | 5/2004 | Asano et al. | |
| 6,743,645 B2 | 6/2004 | Kubota et al. | |
| 6,750,654 B2 | 6/2004 | Sato | |
| 6,771,071 B1 | 8/2004 | Wright et al. | |
| 6,777,934 B2 | 8/2004 | Takahashi et al. | |

(Continued)

FOREIGN PATENT DOCUMENTS

JP    57030943 A    2/1982

(Continued)

OTHER PUBLICATIONS

Boyd M. Goodson; "Advances in Magnetic Resonance—Nuclear Magnetic Resonance of Laser-Polarized Noble Gases in Molecules, Materials, and Organisms"; Journal of Magnetic Resonance; Apr. 2002; pp. 157-216; vol. 155, No. 2; XP004407991; ISSN: 1090-7807; Elsevier Science, USA.

(Continued)

*Primary Examiner*—Brij Shrivastav
*Assistant Examiner*—Megann E. Vaughn

(57) ABSTRACT

Embodiments of the invention relate to a system and method for non-destructively inspecting a component that is at least partially made of a composite material. In one embodiment, the composite component can be a ceramic matrix composite vane or a liner for a turbine engine. Aspects of the invention involve imaging the component using a magnetic resonance imaging (MRI) apparatus. To enhance the image, the component can be infiltrated with at least one contrast media, which can be in liquid or gas form. By imaging the component using the MRI apparatus, internal and/or external defects of the component can be revealed. In addition, internal and/or external features of interest can examined for dimensional accuracy, among other things.

12 Claims, 3 Drawing Sheets

U.S. PATENT DOCUMENTS

| | | |
|---|---|---|
| 6,782,286 B2 | 8/2004 | Miyazaki |
| 2003/0146382 A1 | 8/2003 | Suzuki et al. |
| 2004/0030536 A1 | 2/2004 | Woods et al. |
| 2004/0065826 A1 | 4/2004 | Berger et al. |
| 2004/0089812 A1 | 5/2004 | Favro et al. |
| 2004/0186377 A1* | 9/2004 | Zhong et al. ............ 600/431 |

FOREIGN PATENT DOCUMENTS

| | | |
|---|---|---|
| JP | 58213240 A | 12/1983 |
| JP | 05007569 A | 1/1993 |
| JP | 08261961 A | 10/1996 |
| JP | 08327571 A | 12/1996 |
| JP | 10318951 A | 12/1998 |
| JP | 2000055844 A | 2/2000 |
| WO | WO 02/04972 A1 | 1/2002 |
| WO | WO 02/059586 A2 | 8/2002 |
| WO | WO 03/031956 A1 | 4/2003 |

OTHER PUBLICATIONS

Igor L. Moudrakovski, Stephen Lang, Christopher I. Ratcliffe, Benoit Simard, Giles Santyr, and John A. Ripmeester; "Chemical Shift Imaging with Continuously Flowing Hyperpolarized Xenon for the Characterization of Materials"; Journal of Magnetic Resonance; Jun. 2000; pp. 372-377; vol. 144, No. 2; XP004406924; ISSN: 1090-7807; Academic Press.

C.H. Tseng, G.P. Wong, V.R. Pomeroy, R.W. Mair, D.P. Hinton, D. Hoffmann, R.E. Stoner, F.W. Hersman, D.G. Cory and R.L. Walsworth; "Low-Field MRI of Laser Polarized Noble Gas"; The American Physical Society; Physical Review letters, Oct. 26, 1998; pp. 3785-3788; vol. 81, No. 17; XP002383622; ISSN: 0031-9007.

Anton S. Wallner, William M. Ritchey; "Void Distribution and Susceptibility Differences in Ceramic Materials Using MRI"; Materials Research Society, Mar. 1993; pp. 655-661; vol. 8, No. 3; XP009067269.

S. Karunanithy; "Continuous Examination of SiC Fiber-Reinforced Alumina with MRI, FT-IR, and SEM"; Ceramic Engineering an Science Proceedings; Jan. 14, 1990; pp. 1295-1301; vol. 11, No. 9-10; XP009067290; Westerville, Ohio, USA.

* cited by examiner

INSPECTION OF COMPOSITE COMPONENTS USING MAGNETIC RESONANCE IMAGING

FIELD OF THE INVENTION

The invention relates in general to composite components and, more particularly, to a system and method for inspecting composite components.

BACKGROUND OF THE INVENTION

Composites are a combination of materials differing in composition and/or form to obtain specific characteristics and properties. The constituent materials substantially retain their identities. One type of composite material is a ceramic matrix composite (CMC). A CMC can have a matrix made of a ceramic material and reinforcing fibers made of the same or a different material.

Composite components are difficult to inspect using traditional non-destructive methods, such as thermal, x-ray and ultrasound imaging. While these methods are well suited for materials with distinct differences in some material property, they are not sensitive enough to adequately inspect the features of interest of a composite component. In some cases, the constituent materials of a composite can be identical or substantially identical. For example, an alumina-alumina CMC includes alumina reinforcing fibers in an alumina matrix. Such a material is not amenable to conventional non-destructive inspection methods. Further, composite materials are inherently porous, and they can contain natural air voids. However, one common source of material defects in a composite material is trapped air. Under conventional inspection methods, it is difficult to consistently distinguish unwanted air pockets from natural voids. Thus, there is a need for a system that facilitates the non-destructive inspection and evaluation of composite components.

SUMMARY OF THE INVENTION

In one respect, aspects of the invention relate to an inspection system. The system includes a magnetic resonance imaging machine. The magnetic resonance imaging machine has a scanning system, a signal processing system and a display. The scanning system includes an imaging chamber.

A component is disposed in the imaging chamber. The component is made of a composite material. In one embodiment, the composite component can be made of ceramic matrix composite. The composite component can be at least one of non-magnetic and non-conductive. The composite material can include one of epoxy, glass, carbon, polymer or plastic.

A contrast media is also provided in the imaging chamber. The contrast media can be one of helium, hydrogen, water, and a low viscosity hydrocarbon. A container can be placed inside of the imaging chamber. When provided, the component and the contrast media can be disposed within the container. The scanning system can image the component, and the data generated therefrom can be analyzed by the signal processing system. The image can be presented on the display. The contrast media can enhance at least the external surfaces of the component.

In one embodiment, the composite component can be at least partially porous. Thus, the contrast media can infiltrate the interior pores of the component. As a result, the imaging of internal features of the component can be enhanced. In another embodiment, at least a portion of the component can be hollow. The hollow interior can include at least one internal feature. The contrast media can infiltrate the hollow interior such that imaging of the hollow interior and/or the at least one internal feature of the component can be enhanced.

In some instances, a second contrast media can be provided in the imaging chamber. The contrast media and the second contrast media can be substantially different. The nature of the media and/or the internal features of the component can be discerned by examining the manner in which the contrast media and the second contrast media infiltrate the component.

Aspects of the invention further relate to a non-destructive inspection method. The method includes the steps of: placing an at least partially porous composite component into a magnetic resonance imaging (MRI) machine; scanning the component using the MRI machine; and displaying the scanned image of the component. The displayed image can be examined to one of identify a defect in the component and confirm dimensional accuracy of the component.

In one embodiment, the inspection method can include additional steps such as drawing a vacuum on the composite component so as to substantially evacuate at least some of the pores of the component, and subsequently infiltrating the component with a contrast media so as to substantially fill at least some of the pores in the component with the contrast media. In such case, the scanning and displaying steps can be performed before, during and/or after infiltration with the step of drawing a vacuum.

The component can be subjected to a contrast media such that at least the outer surfaces of the component can be engaged by the contrast media. When the component is at least partially porous, at least some of the pores of the component can be infiltrated with a first contrast media. In such case, the steps of scanning and displaying can be performed before, during and after infiltration with the first contrast media. As a result, the scanning and displaying steps can be enhanced. The contrast media can later be extracted from the component. According to aspects of the invention, the infiltration rate and/or the evacuation rate of the first contrast media can be measured. These rates can then be used to evaluate one or more of the following: material properties of the component, mechanical properties of the component, potential defect features, and known defect features.

In some instances, the method can further include the step of infiltrating the component with a second contrast media so as to substantially fill at least some of the pores in the component with the second contrast media. The first contrast media infiltrating step and the second contrast media infiltrating step can be performed at one of substantially the same time, overlapping times, and non-overlapping times.

DETAILED DESCRIPTION OF EMBODIMENTS OF THE INVENTION

Figure 1:
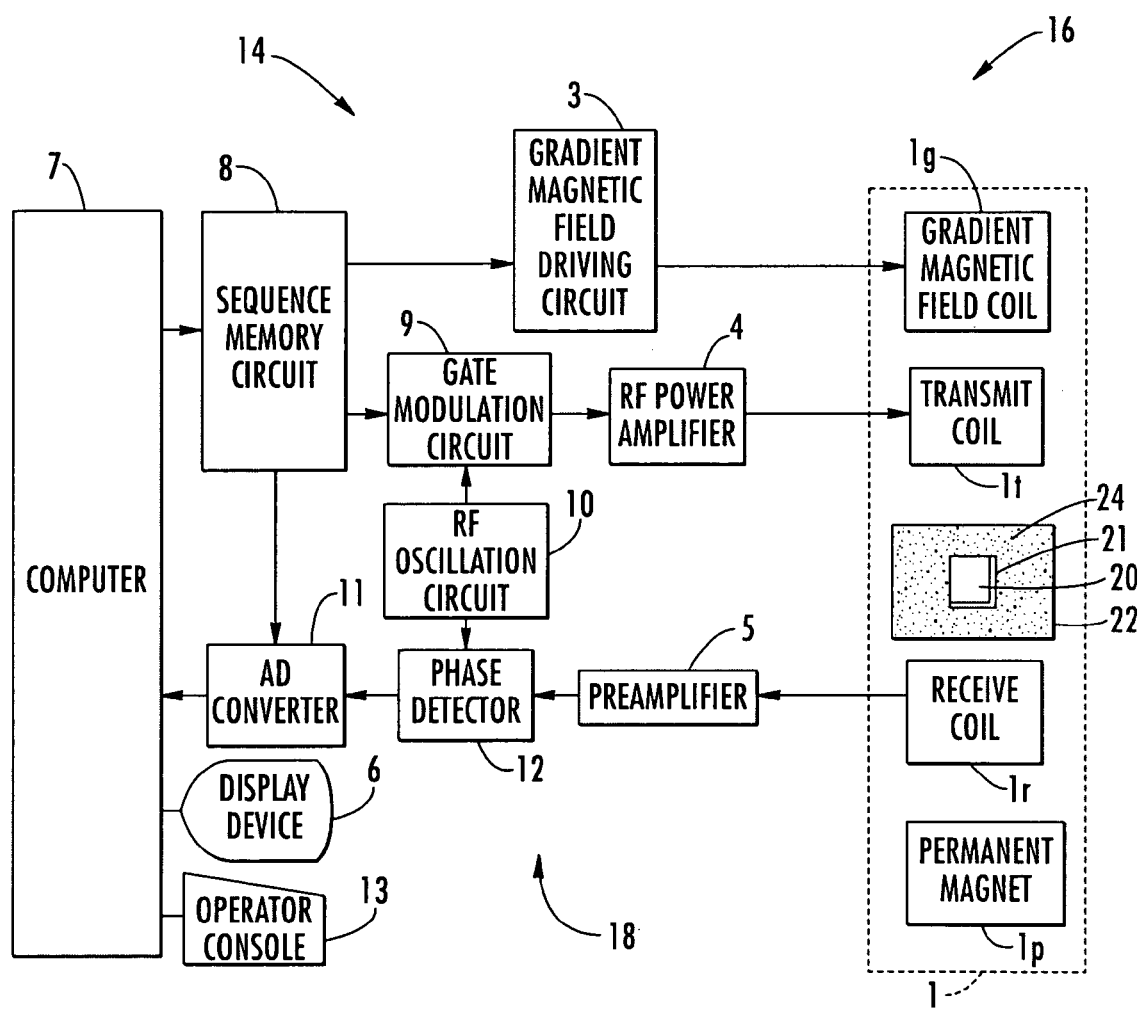
FIG. 1 is a diagrammatic view of an MRI inspection system according to aspects of the invention.
Figure 2:
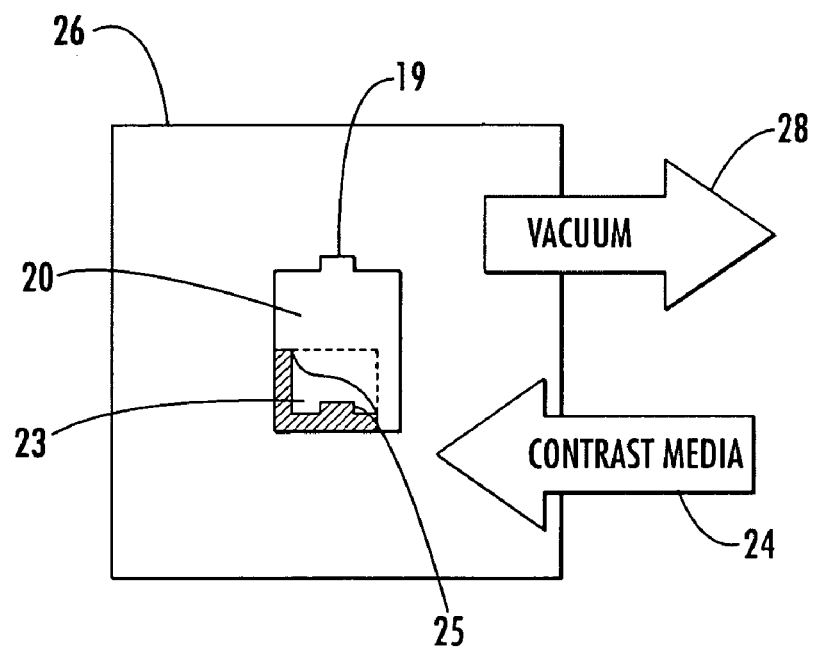
FIG. 2 is a top plan view of a container housing a composite component according to aspects of the invention.
Figure 3:
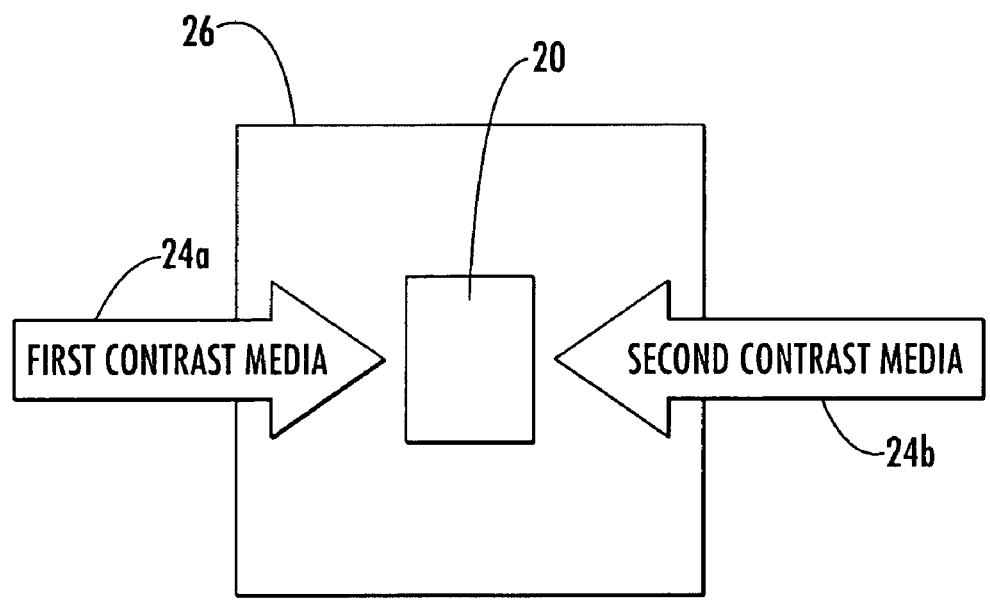
FIG. 3 is a top plan view of the component in the container, showing the container being filled with more than one contrast media according to aspects of the invention.

Embodiments of the present invention address the shortcomings of prior non-destructive inspection methods. Embodiments of the invention will be explained in the context of various possible systems and methods, but the detailed description is intended only as exemplary. Embodiments of the invention are shown in FIGS. 1–3, but the present invention is not limited to the illustrated structure or application.

A system and method according to embodiments of the invention generally involve inspecting a component 20 using magnetic resonance imaging. Aspects of the invention are specifically directed to inspecting a component 20 that is at least partially made of a composite material. The composite material can include epoxy, glass, carbon, ceramic, polymer, or plastic. Non-magnetic and/or non-conductive composites are especially amenable to inspection according to aspects of the invention. The composite can be at least partially porous and, preferably, the composite can be penetrated by a liquid and/or a gas. As shown in FIG. 2, the component 20 can have one or more external surface features 19. In one embodiment, at least a part of the component 20 can be hollow 23 with one or more internal geometric features 25.

Embodiments of an inspection system and method according to aspects of the invention are particularly well suited for ceramic matrix composites (CMC). The component 20 can be made of almost any CMC, but non-magnetic and non-conductive CMCs, such as alumina-alumina, are preferred. Embodiments of the invention are not limited to non-magnetic and non-conductive CMC components 20. For example, embodiments of the invention can be used on a CMC component made of a nonmetallic matrix (i.e., epoxy) reinforced with metal fibers (i.e., aluminum). Further, at least a portion of the component 20 can be covered with a coating 21 such as a thermal insulating material, thermal barrier coating or friable gradable insulation. Such coating are known, and examples of such coatings are disclosed in U.S. Pat. Nos. 6,676,783; 6,641,907; 6,287,511; and 6,013,592, which are incorporated herein by reference.

The component 20 under inspection can be almost any kind of component. For instance, the component 20 can be from aerospace, communications, automotive, and power generation applications, just to name a few possibilities. In one embodiment, aspects of the invention can be used in connection with gas turbine engine components; specifically, the component 20 can be a CMC turbine vane or a CMC combustor liner.

According to embodiments of the invention, the component 20 can be inspected using a magnetic resonance imaging (MRI) machine 14. MRI technology is well known and understood. FIG. 1 shows one example of an MRI apparatus 14 that can be used according to aspects of the invention. Generally, the MRI machine 14 can have a scanning system 16, a signal processing system 18 and a display 6.

The scanning system 16 of the MRI machine 14 can include a magnet assembly 1 having a bore or imaging chamber 22 for receiving the component 20 therein. A table or a fixture (not shown) can be provided within the imaging chamber 22 for supporting the component 20. The magnet assembly 1 can further include a permanent magnet $1p$, gradient magnetic field coil $1g$, a transmit coil $1t$ and a receive coil $1r$. The permanent magnet $1p$ can apply a static magnetic field having a constant strength to the component 20. It should be noted that a super- or normal-conductive magnet can be employed in place of the permanent magnet type magnet $1p$. The gradient magnetic field coil $1g$ can apply gradient pulses to a slice axis, phase axis and frequency axis. The transmit coil $1t$ can supply RF pulses for exciting spins of atomic nuclei within the component 20. The receive coil $1r$ can detect MR signals from the component 20. These components can be disposed so as to substantially surround the imaging chamber 22.

The gradient magnetic field coil $1g$, transmit coil $1t$, and receive coil $1r$ can be operatively associated with a gradient magnetic field driving circuit 3, an RF power amplifier 4, and a preamplifier 5, respectively. A sequence memory circuit 8 can operate the gradient magnetic field driving circuit 3 based on a stored pulse sequence in response to instructions from a computer 7 to thereby apply gradient pulses from the gradient magnetic field coil $1g$ in the magnet assembly 1. The sequence memory circuit 8 can also operate a gate modulation circuit 9 to modulate a carrier output signal from an RF oscillation circuit 10 into a pulsed signal of predefined timing and envelope shape. The pulsed signal can be applied to the RF power amplifier 4 as an RF pulse, power-amplified in the RF power amplifier 4, and then applied to the transmit coil $1t$ in the magnet assembly 1 to selectively excite a desired slice region.

As noted above, the MRI machine 14 can include a signal processing system 18. The signal processing system 18 can include the preamplifier 5, which can amplify the MR signals from the component 20 detected at the receive coil $1r$ in the magnet assembly 1. The preamplifier 5 can input the signal to a phase detector 12. The phase detector 12 can phase-detect the MR signals from the preamplifier 5 employing the carrier output signal from the RF oscillation circuit 10 as a reference signal, and can supply the phase-detected signal to an A/D converter 11. The A/D converter 11 can convert the phase-detected analog signal into a digital signal, and can input it to the computer 7.

The computer 7 can read or process the data from the A/D converter 11, and can perform image reconstruction calculation to produce an image of the desired slice region. The computer can be operatively associated with a display 6. Thus, the image can be displayed on a display device 6. The display 6 can be, for example, a printer or a monitor. The computer 7 can also be responsible for overall control such as receiving information supplied from an operator console 13.

Again, the MRI machine 14 shown in FIG. 1 is provided as an example, and it will be understood that embodiments of the invention are not limited to the MRI machine 14 shown in FIG. 1. It will be understood that an MRI machine 14 according to aspects of the invention can include additional components to those shown in FIG. 1 or may not include every component shown in FIG. 1. Indeed, aspects of the invention can be used in connection with any MRI machine, such as those disclosed in U.S. Pat. Nos. 6,782,286; 6,777,934; 6,771,071; 6,750,654; 6,728,568; 6,714,807; 6,611,144; and 6,600,317, which are incorporated herein by reference.

In some instances, it may be desirable or necessary to enhance the MRI image of the component 20 to facilitate the inspection of key features and defects. To that end, the component 20 can be infiltrated with a contrast media 24. The contrast media 24 can be provided in gas or liquid form. Examples of gaseous contrast media can include helium and hydrogen. Liquid contrast media can be water or a low viscosity hydrocarbon. It will be appreciated that the contrast media can be particularly beneficial when used in connection with composite components 20 that are gas or liquid permeable.

A contrast media 24 according to aspects of the invention can be selected based on a number of characteristics. Naturally, the contrast media 24 should not be one that can harm or react with the component 20 under inspection. In addition, the contrast media 24 should be detectable by an MRI machine 14. Another characteristic that should be considered is mobility of the contrast media 24. Mobility can be a function of at least particle size and kinetics. The smaller the individual particles of the contrast media 24, the more mobile the contrast media 24 is likely to be. For example, helium and hydrogen can be good candidates for the contrast media 24 because their atoms are small. As for kinetics, the higher the temperature of the contrast media 24, the greater the kinetic action within the contrast media 24, thereby facilitating diffusion of the contrast media 24 into the component 20.

In the context of a liquid contrast media, mobility can be a function of the viscosity of the liquid. Low viscosity liquids can penetrate the component 20 more easily than high viscosity liquids. Likewise, low viscosity liquids are easier to remove from the component 20. Other mobility characteristics germane to liquid contrast media are surface tension or wetting. That is, certain materials do not wet easily. Thus, when a liquid contrast media is introduced into the component 20, it is desirable that the liquid contrast media has a low contact angle so as to wet easily and to enter small cavities or pores in the component 20 by capillary action.

Having described the individual components of an inspection system according to embodiments of the invention, various manners of inspecting the composite component 20 will now be described. The following methods are provided merely as examples, and embodiments of the invention are not intended to be limited to the methods described. It will be understood that additional steps can be performed, and not every step discussed need occur.

In one embodiment, the component 20 can be placed inside of the imaging chamber 22 in the MRI scanning system 16. The scanning system 16 can be operated so as to image the component 20 along any plane passing through the component 20. The data received from the MRI scanning system 16 can be received and processed by the signal processing system 18. The data can be presented for viewing on the display 6.

In another embodiment, the component 20 can be infiltrated with the contrast media 24 prior to being imaged by the MRI scanning system 16. Infiltration of the component 20 with the contrast media 24 can be achieved in several ways. In one embodiment, the imaging chamber 22 of the MRI scanning system 16 can be filled with the contrast media 24, particularly in the form of a gas. The contrast media 24 can infiltrate the component 20 by diffusion or capillary action.

Alternatively, the component 20 can be placed inside of a container 26, as shown in FIG. 2. The container 26 can be filled with the contrast media 24 in liquid or in gas form. The container 26 can be placed inside of the imaging chamber 22 of the MRI scanning system 16 for imaging. The container 26 can be any size or shape. The container 26 can be opened or closed. The container 26 can be made of any material so long as the material of the container 26 can be sufficiently distinguished by the MRI machine 14 from the material of the component 20 and so long as the material of the container 26 does not otherwise confound the imaging of the component 20. Preferably, the container 26 is virtually transparent to the MRI machine 14 or at least readily distinguishable from the component 20 and contrast media 24. In one embodiment, the container 26 can be a plastic bag.

Again, the contrast media 24 may not be used in all instances. For instance, the contrast media 24 may be reserved for situations in which it is difficult to discern the nature of a feature in an MRI image, such as whether a particular feature is a defect. It should be noted that the contrast media 24 can be used even if the component 20 is non-permeable. In such case, the contrast media 24 can be used to enhance the image of the component 20 so a geometric map of the external features of the component 20 can be created. In addition, if the component 20 is hollow 23 with internal geometric features 25, the contrast media 24 can be used to enhance the image of the component 20 so a geometric map of the internal features 23 of the component 20, including the hollow cavity 23, can be created.

After completion of testing, the contrast media 24 can be removed from the component 20 in any of a number of ways. For example, the contrast media 24 can be allowed to exit through diffusion, or the contrast media 24 can be dried or baked out of the component 20.

Diffusion of the contrast media 24 into the component 20 not only involves penetrating the component 20, but also displacing whatever already fills the internal pores of the component 20, such as air. Thus, embodiments of the invention can be configured to facilitate infiltration of the component 20 with the contrast media 24. For instance, the contrast media 24 can be pressurized to force the contrast media 24 into the component 20. Alternatively, prior to immersing the component 20 in the contrast media 24, a vacuum 28 can be drawn on the component 20 while it is inside of the MRI scanner 16 or before the component 20 is placed inside of the MRI scanner 16. Further, the vacuum 28 can be drawn when the component 20 is in the container 26 to remove substantially all of the air from the component 20, as shown in FIG. 3. MRI inspection can be conducted before, during, and after the vacuum 28 is drawn on the component 20.

As a result of drawing a vacuum 28, the component 20 can become sponge-like with a plurality of vacuum holes. Then, the imaging chamber 22 or the container 26 can be backfilled with the contrast media 24, which can now permeate relatively quickly into the pores of the component 20. In either case, once the contrast medium sufficiently infiltrates the component 20, the component 20 can be imaged by the MRI apparatus 14. Once the inspection is finished, a vacuum 28 can be drawn on the component 20 to facilitate extraction of the contrast media 24 from the component 20.

Further, it should be noted that, in some instances, the component 20 can be infiltrated with more than one contrast media 24 to further assist in the characterization of the internal features of interest in the component 20. For instance, as shown in FIG. 3, the component 20 can be infiltrated by a first contrast media 24a and a second contrast media 24b. Ideally, each contrast media 24a, 24b would be selected based on the ability of the MRI machine 14 to distinguish between them. It is also preferred if the contrast media 24a, 24b are substantially different in some respect, such as having different mobility characteristics. For example, the first contrast media 24a can be a high diffusion media, such as helium, and the second contrast media 24b can be highly wetting. For two or more liquid contrast medias, the contrast media 24a, 24b can have substantially different viscosities.

The contrast media 24a, 24b can be used in parallel or in series with each other. For instance, the component 20 can be exposed to the first and second contrast media 24a, 24b at substantially the same time. Alternatively, the component 20 can be exposed to the first and second contrast media 24a, 24b at different times, which may or may not overlap. In one embodiment, a vacuum 28 can be drawn on the component 20. Next, the component 20 can be infiltrated by the first contrast media 24a. MRI imaging can be conducted before, during and after the infiltration of the first contrast media 24a. A vacuum 28 can again be drawn on the component 20 so as to substantially remove the first contrast media 24a from the component 20. At that point, the component 20 can be infiltrated with the second contrast media 24b. Again, MRI imaging can be performed before, during and after the infiltration of the second contrast media 24b. Once inspection has been completed, the second contrast media 24b can be removed from the component 20, by the vacuum 28 or otherwise. It should be noted that MRI inspection of the component 20 can be performed before, during and/or after any of the instances in which the vacuum 28 is drawn on the component 20. Further, in any of the above methods, the infiltration and/or the evacuation rates of the contrast media 24a, 24b can be used to evaluate material and/or mechanical properties as well as potential or known defect features.

In one embodiment, the size and nature of a feature of interest, such as a void, can be judged by using the MRI machine 14 to compare the amount of time it takes for one contrast media 24a to fill the void as compared to the other contrast media 24b. Such features can also be evaluated by using the MRI machine 14 to assess the rate of displacement or replacement between the media 24a, 24b.

It should be noted that any of the MRI inspection of the composite component 20 can be performed at various times to further ascertain the nature of internal features of interest based on, among other things, mobility of the contrast media 24. For instance, MRI inspection can be conducted before, during, and after infiltration of the composite component 20 with the contrast media 24.

Similarly, MRI inspection according to aspects of the invention can be done at various stages of the manufacturing process. For example, the component 20 can be inspected before and after it is assembled with other components. Further, the component 20 can be tested before and after a period of use. In addition, the component 20 can be inspected prior to and after application of a coating material 21 over the component 20. Further, the component 20 can be inspected while being subjected to mechanical stress or a thermal load, or such inspection can occur when the component 20 is not subjected to any loading. When the component 20 is made of CMC, MRI inspection can occur prior to and after sintering the individual laminates together.

An inspection system and method according to aspects of the invention can be used to detect various things, such as defects in the component 20 and geometric features of interest. Examples of defects in the composite component 20 that may be of interest include but are not limited to: delamination, missing reinforcements, porosity in the matrix, unbonded matrix and reinforcement, unbonded outer coating (i.e., FGI) to the component, porosity in an outer coating, cracking or fractures in the matrix or outer coating, and oxidation damage. Aspects of the invention can be used to examine and confirm dimensional accuracy of internal and external geometric features of the composite component 20. For example, the size, shape and location of features (holes, slots, threads, cooling channels, etc.) can be confirmed using an inspection system and method according to aspects of the invention. Further, aspects of the invention can be used to create a geometric map of the external features of the component.

The foregoing description is provided in the context of one possible MRI inspection system and method. It will of course be understood that the invention is not limited to the specific details described herein, which are given by way of example only, and that various modifications and alterations are possible within the scope of the invention as defined in the following claims.

What is claimed is:

1. An inspection system comprising:
   a magnetic resonance imaging machine having a scanning system, a signal processing system and a display, the scanning system including an imaging chamber;
   a component made of an alumina ceramic matrix composite material, the component being disposed in the imaging chamber; and
   a contrast media provided in the imaging chamber,
   wherein the component is imaged by the scanning system and the data generated therefrom is analyzed by the signal processing system, wherein the image is presented on the display, whereby the contrast media enhances at least the external surfaces of the component.

2. The system of claim 1 wherein the contrast media is one of helium, hydrogen, water, and a low viscosity hydrocarbon.

3. The system of claim 1 further including a second contrast media, wherein the contrast media and the second contrast media are substantially different, whereby the nature of the media and/or the internal features of the component can be discerned by the manner in which the contrast media and the second contrast media infiltrate the component.

4. The system of claim 1 wherein at least a portion of the component is hollow, wherein the hollow interior includes at least one internal feature, wherein the contrast media infiltrates the hollow interior, whereby imaging of the hollow interior of the component is enhanced.

5. The system of claim 1 further including a container placed inside of the imaging chamber, wherein the component and the contrast media are disposed within the container.

6. The system of claim 1 wherein the composite component is at least partially porous, wherein the contrast media infiltrates the interior pores of the component, whereby the imaging of internal features of the component is enhanced.

7. The system of claim 1 the composite component is at least one of non-magnetic and non-conductive.

8. The system of claim 1 wherein the composite material includes one of epoxy, glass, carbon, polymer or plastic.

9. The system of claim 1 wherein the composite alumina ceramic material comprises an alumina-alumina ceramic matrix coposite composition.

10. The system of claim 9 wherein the composite alumina ceramic material comprises alumina reinforcing fibers in an alumina matrix.

11. The system of claim 10, wherein the composite alumina ceramic material is coated with a thermal coating.

12. An inspection system comprising:
    a magnetic resonance imaging machine having a scanning system, a signal processing system and a display, the scanning system including an imaging chamber;
    a component made of a composite material, the component being disposed in the imaging chamber;

a first contrast media provided in the imaging chamber; and a second contrast media provided in the imaging chamber, wherein the component is imaged by the scanning system and the data generated therefrom is analyzed by the signal processing system, wherein the image is presented on the display, whereby the contrast media enhances at least the external surfaces of the component wherein the first contrast media and the second contrast media are substantially different, whereby the nature of the media and/or the internal features of the component can be discerned by the manner in which the contrast media and the second contrast media infiltrate the component.

* * * * *